US010449219B2

(12) United States Patent
Law

(10) Patent No.: US 10,449,219 B2
(45) Date of Patent: Oct. 22, 2019

(54) DISEASE PREVENTION AND ALLEVIATION BY HUMAN MYOBLAST TRANSPLANTATION

(71) Applicant: Peter K Law, Richmond Hill (CA)

(72) Inventor: Peter K Law, Richmond Hill (CA)

(*) Notice: Subject to any disclaimer, the term of this patent is extended or adjusted under 35 U.S.C. 154(b) by 0 days.

(21) Appl. No.: 15/690,803

(22) Filed: Aug. 30, 2017

(65) Prior Publication Data

US 2018/0000867 A1    Jan. 4, 2018

Related U.S. Application Data

(62) Division of application No. 13/968,982, filed on Aug. 16, 2013, now abandoned.

(51) Int. Cl.
| | | |
|---|---|---|
| *C12N 5/00* | (2006.01) | |
| *C12N 5/02* | (2006.01) | |
| *C12Q 1/68* | (2018.01) | |
| *A61K 35/34* | (2015.01) | |
| *G01N 33/50* | (2006.01) | |
| *C12N 5/077* | (2010.01) | |
| *A61K 39/00* | (2006.01) | |

(52) U.S. Cl.
CPC ............. *A61K 35/34* (2013.01); *A61K 39/00* (2013.01); *C12N 5/0658* (2013.01); *G01N 33/5008* (2013.01); *C12Q 1/68* (2013.01); *G01N 2800/042* (2013.01); *G01N 2800/2878* (2013.01); *G01N 2800/324* (2013.01)

(58) Field of Classification Search
CPC ........ A61K 35/34; C12N 5/0658; C12Q 1/68; G01N 33/5008
USPC .................................. 435/6.1, 325, 375, 378
See application file for complete search history.

(56) References Cited

U.S. PATENT DOCUMENTS

| | | |
|---|---|---|
| 5,130,141 A | 7/1992 | Law |
| 6,261,832 B1 | 7/2001 | Law |
| 7,166,279 B2 | 1/2007 | Law |
| 7,341,719 B1 | 3/2008 | Law |
| 2002/0031501 A1 | 3/2002 | Law |
| 2003/0232431 A1 | 12/2003 | Law |
| 2005/0244384 A1 | 11/2005 | Law |
| 2006/0057119 A1 | 3/2006 | Law |

FOREIGN PATENT DOCUMENTS

| | | |
|---|---|---|
| WO | WO9618303 | 6/1996 |
| WO | WO0228470 | 4/2002 |
| WO | WO2004014302 | 2/2004 |
| WO | WO2004030706 | 4/2004 |
| WO | WO2005020916 | 3/2005 |

OTHER PUBLICATIONS

Wu et al., 2012, Aging Research reviews, vol. 11, p. 32-40.*
Agrahari et al., 2017, Expert Opinion on Drug Delivery, vol. 14, No. 10, p. 1145-1162.*
Moisset et al., 1998, Biochemical and Biophysical Research Communications, vol. 247, p. 94-99.*
Abdelwahid et al., 2011, Current Cardiology Reviews, vol. 7, p. 201-212.*
Tremblay et al., 2010, Pediatric Transplantation, 14: 813-819.*
Law, Peter, 2002, US 20020031501 A1.*
Ye et al., 2009, Diabetologia, vol. 52, p. 1925-1934.*
Law, Peter K. et al. "Normal Myoblast Injections Provide Genetic Treatment for Murine Dystrophy", Muscle & Nerve, Genetic Treatment of Dystrophy, Jun. 1988, pp. 525-533.
Law, Peter K. et al. "Histoincompatible Myoblast Injection Improves Muscle Structure and Function of Dystrophic Mice", Transplantation Proceedings, vol. XX, No. 3, Suppl. Jun. 3, 1988, pp. 1114-1119.
Law, Peter K. et al. "Pathogenesis and Treatment of Hereditary Muscular Dystrophy", Dept. of Neurology and Physiology/Biophysics, Univ. of TN, Memphis TN, 1990, pp. 101-118.
Law, Peter K. et al. "Myoblast Transfer Improves Muscle Genetics/Structure/Function and Normalizes the Behavior and Life-Span of Dystrophic Mice", Depts. of Neurology and Physiology/Biophysics Univ. of TN, Memphis, TN, 1990, pp. 74-87.
Law, Peter K. et al. "Plausible Structural/Functional/Behavioral/Biochemical Transformations following Myoblast Transfer Therapy", Depts. of Neurology and Physiology/Biophysics Univ. of TN, Memphis, TN, 1990, pp. 240-251.
Law, Peter K. et al. Myoblast Transfer: Gene Therapy for Muscular Dystrophy, R.G. Landes Company, Austin, Memphis, Tennessee, 1994.
Fang, Qiuwen et al. "Vital marker for muscle nuclei in myoblast transfer", Departments of Neurology and Physiology and Biophysics Univ of TN, Memphis, TN, May 10, 1990, pp. 49-52.
Chen, Ming et al. "Dystrophin Cytochemistry in mdx Mouse Muscles Injected with Labeled Normal Myoblasts", Cell Therapy Research Foundation, Memphis, TN, pp. 17-22.
Law, P.K. et al. "Myoblast Injection Method Regulates Cell Distribution and Fusion", Transplantation Proceedings, vol. 26, No. 6, Dec. 1994, pp. 3417-3418.
Fang, Q. et al. "MHC-I Antigens on Cultured Human Myoblasts", Transplantation Proceedings, vol. 26, No. 6, Dec. 1994, pp. 3487.
Law, Peter K. "Methods for Human Myoblast Culture and Transplantation", Methods in Cell Transplantation, Landes Company, 1995, pp. 707-734.
Law, P. et al."World's First Human Myoblast Transfer into the Heart", Frontiers in physiology, Joint Meeting, Stockholm, Sweden, Aug. 16-19, 2000, the City of Stockholm.

(Continued)

*Primary Examiner* — Shin Lin Chen
(74) *Attorney, Agent, or Firm* — Sughrue Mion, PLLC

(57) ABSTRACT

Methods and materials are described for human genome prophylaxis and therapy of diseases using myoblast transfer. These methods result in gene transcript changes in multiple pathways. Linking the myoblast transfer technology development from DMD, cardiomyopathy, and Type-II diabetes, the myoblast transfer demonstrably mediates its effect through transfer of the normal myoblast nuclei that supply the complete human genome, in addition to just replenishing the missing gene(s) or the aberrant gene(s). The replacement genes then transcribe to produce the necessary proteins or factors for genetic repair. A variety of uses of this technology are described, including that for disease treatment, disease prevention, drug discovery, and selection of superior cells and clones for therapy.

9 Claims, 2 Drawing Sheets

(56) References Cited

OTHER PUBLICATIONS

Law, P. et al. "World's First Human Myoblast Transfer into the Heart", Acts Physiol Scan 2000, 170, A1-A114, 2000 Scandinavian Physiological Society, p. A17.
Law, Peter K. et al. "Human VEGF165-myoblasts produce concomitant angiogenesis/myogenesis in the regenerative heart", Molecular and Cellular Biochemistry, Netherlands, 2004, 263: pp. 173-178.
Law, P. et al. "Mechanisms of Myoblast Transfer in Treating Heart Failure", 8th World Congress on Heart Failure, International Academy of Cardiology, Advances in Heart Failure, pp. 43-48.
Law, Peter K. "Concomitant Angiogenesis/Myogenesis in the Regenerative Heart", Genomics/Pharmacogenomics, Business Briefing: Future Drug Discovery 2003, pp. 64-67.
Haider, Husnain Kh. et al. "Avoiding Compliance With Histocompatibility Dogma Using Immune Privileged Cell Xenografts", 2003 by The Society of Thoracic Surgeons , Published by Elsevier Inc., pp. 339-340.
Sim, Eugene K. et al. "Single fiber skeletal muscle transplantation or purified myoblast engraftment?", The Journal of Thoracic and Cardiovascular Surgery ● vol. 125, No. 5 1181, May 2003, pp. 1181-1182.
Haider, Husnain Kit et al. "Myoblast Transplantation for Cardiac Repair Using Transient Immunosuppression", Department of Cardiothoracic and Vascular Surgery, National University of Singapore, Singapore and (1) Cell Therapy Research Foundation, Memphis, USA, Basic Appl Myol 13 (1): 2003, pp. 45-52.
Haider, H.Kh. et al. "Effectiveness of Transient Immunosuppression Using Cyclosporine for Xenomyoblast Transplantation for Cardiac Repair", Transplantation Proceedings, 36, 2004, pp. 232-235.
Haider, Husnain Kh. et al. "Angiomyogenesis for cardiac repair using human myoblasts as carriers of human vascular endothelial growth factor", J Mol Med, 2004, pp. 539-549.
Xiao, Yong-Fu et al. "Immunosuppression and Xenotransplantation of Cells for Cardiac Repair", The Society of Thoracic Surgeons, 2004, pp. 737-744.
Ye, Lei et al. "High efficiency transduction of human VEGF165 into human skeletal myoblasts: in vitro studies", Experimental and Molecular Medicine, vol. 35, No. 5, Oct. 2003, pp. 412-420.
Ye, Lei et al. "Reversal of myocardial injury using genetically modulated human skeletal myoblasts in a rodent cryoinjured heart model", The European Journal of Heart Failure 7 (2005) pp. 945-952.
Law, Peter K. Singapore Patent No. 9704642-9, Title: Instrument for Cell Culture, Issued Dec. 14, 2001.
Ye, Lei et al. "Improved angiogenic response in pig heart following ischaemic injury using human skeletal myoblast simultaneously expressing VEGF165 and angiopoietin-1", European Journal of Heart Failure 9 (2007) pp. 15-22.
Ye, Lei et al. "Transplantation of Nanoparticle Transfected Skeletal Myoblasts Overexpressing Vascular Endothelial Growth Factor-165 for Cardiac Repair", Downloaded from circ.ahajournals.org at National University of Singapore on Sep. 10, 2007, pp. i113-i120.
Ye, Lei et al. "Nonviral Vector-Based Gene Transfection of Primary Human Skeletal Myoblasts", 2007 by the Society for Experimental Biology and Medicine, pp. 1477-1487.
Ye, Lei et al. "Angiomyogenesis using liposome based vascular endothelial growth factor-165 transfection with skeletal myoblast for cardiac repair", Biomaterials 29 (2008), pp. 2125-2137.
Ye, L. et al. "Skeletal myoblast transplantation for attenuation of hyperglycaemia, hyperinsulinaemia and glucose intolerance in a mouse model of type 2 diabetes mellitus", Diabetologia (2009) 52:pp. 1925-1934.
Ye, Lei et al. "Liposome-based vascular endothelial growth factor-165 transfection with skeletal myoblast for treatment of ischaemic limb disease", J. Cell. Mol. Med. vol. 14, No. 1-2, 2010 pp. 323-336.
Ye, Lei et al. Role of Thymosin?4 on Skeletal Myoblast Migration, Proliferation, and Survival, May 2012, DOI: 10.2174/221029731120200146.
Ma, Jian-Hua et al. "Skeletal myoblast transplantation on gene expression profiles of insulin signaling pathway and mitochondrial biogenesis and function in skeletal muscle", Diabetes Research and Clinical Practice 102, 2013, pp. 43-52.
Law, Peter K. et al. "World's First Myoblast Treatment of Human Cancer Found Safe and Efficacious", Open Journal of Regenerative Medicine, 2017, 6, pp. 1-16.
Law, Peter K. et al. Dystrophin production induced by myoblast transfer therapy in Duchenne muscular dystrophy, The Lancet, Jul. 14, 1990, vol. 336, pp. 114-115.
Law Peter K. et al. Myoblast Transfer Therapy for Duchenne Muscular Dystrophy, Dept. of Neurology, Univ. of TN, Memphis, TN, Acta Pediatr Jpn 1991; 33, pp. 206-215.
Law, P.K. et al. Long-Term Improvement in Muscle Function, Structure and Biochemistry Following Myoblast Transfer in DMD, Acta Cardiomiologica, vol. III, No. 3, 1991, pp. 279-299.
Law, Peter K. et al. Feasibility, Safety, and Efficacy of Myoblast Transfer Therapy on Duchenne Muscular Dystrophy Boys, Cell Transplantation, 1992, vol. 1, pp. 235-244.
Law, Peter K. "Myoblast Transplantation", AAAS, Science, vol. 257, Sep. 4, 1992, pp. 1329-1330.
Law, Peter K. et al. "Myoblast Transfer Therapy for Duchenne Muscular Dystrophy", Advances in Clinical Neurosciences, 1992; 2: Publication 30, pp. 463-470.
Law, Peter K. "Myoblast transfer therapy", The Lancet, vol. 341: Jan. 23, 1993, pp. 247.
Law, Peter K. et al. "Cell Transplantation as an Experimental Treatment for Duchenne Muscular Dystrophy", Cell Transplantation, vol. 2, 1993, pp. 485-505.
Law, P. et al. "Whole Body Myoblast Transfer", Transplantation Proceedings, vol. 26, No. 6, Dec. 1994, pp. 3381-3383.
Law, Peter K. et al. "Myoblast Transfer Therapy for Duchenne Muscular Dystrophy", Acta Paediatr Jpn 1991; 33:, pp. 206-215.
Law, Peter K. et al. "First Human Myoblast Transfer Therapy Continues to Show Dystrophin After 6 Years", Cell Transplantation, vol. 6, No. 1, 1997, pp. 95-100.
Law, P.K. et al. "Human Gene Therapy With Myoblast Transfer", Transplantation Proceedings, 29, 1997, pp. 2234-2237.
Law, Peter et al. "Myoblast transfer as a platform technology of gene therapy", Gene Therapy and Molecular Biology, vol. 1, Mar. 1998, pp. 345-363.
Law, Ph.D, Peter. "Myoblast Transfer as a Platform Technology for Gene Therapy", Technology, Regulatory Affairs Focus, Oct. 1999, pp. 25-27.
Global Dossier, EU App. No. 2837683.
Human Myoblast Genome Therapies and Devices in Regenerative Medicine, Recent patents on Regenerative Medicine, vol. 1, No. 1, pp. 88-117 (2011).
Law, Peter K. "Nuclear Transfer and Human Genome Therapy", Genomics, Business Briefing Future Drug Discovery, pp. 38-42.
Law, Dr. Peter K. "The Regenerative Heart", Business Briefing Pharmatech 2002, pp. 1-5.
Shujia, MD, Jiang et al. "Human Skeletal Myoblasts: Potential for Improving Outcome of Patients with End-Stage Heart Failure", no date.
Abstracts, Angiography & Interventional Cardiology, JACC, Mar. 3, 2004, pp. 39A.
Law, Peter K. et al. "17. Myoblast Genome Therapy and the Regenerative Heart", Cardiovascular Cell CH17, Aug. 18, 2003, pp. 243-258.
Law, Peter K. et al. "The Wor ld's First Myoblast Study of Type II Diabetic Patients", Business Briefing, North American Pharmacotherapy, 2004, Issue 2, pp. 1-2.
Sim, EK et al. "Myoblast transplantation on the beating heart.", Int. Surg., Jul.-Aug. 2005, 90(3), pp. 148-150.
Ye, L. et al. "Liposome-based Vascular Endothelial Growth Factor-165 Transfection with Skeletal Myoblast for Treatment of Ischaemic Limb Disease", Journal of Cellular and Molecular Medicine, Jan.-Feb. 2010, pp. 1-2.
Law, Peter K. et al. "Symposium: Heart cell therapy", Journal of Geriatric Cardiology, Sep. 2006, vol. 3, No. 3, pp. 131-151.
Law, Peter K. et al. "Human myoblast genome therapy", Journal of Geriatric Cardiology, Sep. 2006, vol. 3, No. 3, pp. 135-151.

(56) References Cited

OTHER PUBLICATIONS

Guo, Changfa et al. "Myoblast-based cardiac repair: Xenomyoblast versus allomyoblast transplantation", The Journal of Thoracic and Cardiovascular Surgery, Nov. 2007, pp. 1332-1339.

Law, Peter K. et al. Myoblast Transfer Therapy for Duchenne Muscular Dystrophy:, Acta Paediatr Jpn 1992; 33:, pp. 206-215.

Law, Peter K. et al. Practical Handbook of Advanced Interventional Cardiology, Third Edition, Tips and Tricks, Chapter 30: Delivery of Biologics for Angiogenesis and Myogenesis, no date, pp. 584-597.

Law, Peter K. et al. "Human Myoblast Genome Therapies and Devices in Regenerative Medicine", Recent Patents on Regenerative Medicine 2011, 1, pp. 88-117.

Law, Peter K. et al. "Therapeutic angiomyogenesis using human non-viral transduced VEGF 165myoblasts", Open Journal of Regerative Medicine, vol. 1, No. 1, 2012, pp. 1-9.

Law, Peter K. "Disease Prevention and Alleviation by Human Myoblast Transplantation", Open Journal of Regenerative Medicine, 2016, pp. 25-43.

Law, Peter K. et al. "Myoblasts provide safe and effective treatments for hereditary muscular dystrophies, cardiomyopathies, type 2 diabetes, solid tumors, and aging", https://doi.org/10.1515/9783110587043-004, no date, pp. 72-96.

Miller, MD, R. G. et al. "Myoblast Implantation in Duchenne Muscular Dystrophy: The San Francisco Study", Muscle & Nerve, Apr. 1997, pp. 469-478.

Menasche, MD, PhD, Philippe et al. "The Myoblast Autologous Grating in Ischemic Cardiomyopathy (MAGIC) Trial—First Randomized Placebo-Controlled Study of Myoblast Transplantation", downloaded Nov. 1, 2017, http://circ.ahajournals.org, pp. 1189-1201.

Ben-Dor, MD, Itsik et al. "Potential Hazards and Technical Considerations Associated With Myocardial Cell Transplantation Protocols for Ischemic Myocardial Syndrome", Journal of the American College of Cardiology, 2006, vol. 48, No. 8, pp. 1519-1526.

Edwards, MD, Scott G. et al. "Autologous Blood Injections for Refractory Lateral Epicondylitis", The Journal of Hand Surgery, vol. 28A, No. 2, Mar. 2003, pp. 272-278.

Creaney, Leon et al. "Growth Factor Delivery Methods in the Management of Sports Injuries: The State of Play", Br. J. Sports Med. published online Nov. 5, 2007, pp. 1-16.

* cited by examiner

Figure 1.

| Genes | Accession no. | Categories | Fold change | | |
|---|---|---|---|---|---|
| | | | A | B | C |
| Acaca | NM_133360 | Target genes for SREBP1 | 2.06↑ | 2.87↑ | 0.94 |
| Acox1 | NM_015729 | Lipid Metabolism, Target genes for PPARγ | 11.23↑ | 1.09 | 1.84 |
| Aebp1 | NM_009636 | Transcription Factors and Regulators | 9.06↑ | 2.01↑ | 1.71 |
| Braf | NM_139294 | MAPK Pathway | 2.5↑ | 0.84 | 2.25↑ |
| Cebpa | NM_007678 | Cell Growth and Differentiation Protein Metabolism Transcription Factors and Regulators | 2.64↑ | 1.47 | 1.36 |
| Cfd | NM_013459 | Target genes for PPARγ | 2.27↑ | 4.29↑ | 1 |
| Frap1 | NM_020009 | PI-3 Kinase Pathway Protein Metabolism | 11↑ | 1.25 | 2.81↑ |
| Frs2 | NM_177798 | Cell Growth and Differentiation Insulin Receptor-associated Proteins Protein Metabolism | 4.2↑ | 0.91 | 0.79 |
| Gab1 | NM_021356 | Insulin Receptor-associated Proteins MAPK Pathway Protein Metabolism | 5.62↑ | 0.7 | 0.86 |
| Gpd-1 | NM_010271 | Carbohydrate Metabolism Target genes for PPARγ | 9.38↑ | 2.41↑ | 2.51↑ |
| Hras1 | NM_008284 | Cell Growth and Differentiation MAPK Pathway Protein Metabolism | 3.03↑ | 1.05 | 1.92 |
| Igf2 | NM_010514 | Cell Growth and Differentiation | 19.7↑ | 1.92 | 3.51↑ |
| Irs2 | NM_001081212 | Cell Growth and Differentiation Insulin Receptor-associated Proteins | 2.48↑ | 1.23 | 1.09 |
| Jun | NM_010591 | Cell Growth and Differentiation Primary Target Genes for Insulin Signaling Protein Metabolism Transcription Factors and Regulators | 2.93↑ | 2.01↑ | 1.05 |
| Leptin | NM_008493 | Lipid metabolism Carbohydrate Metabolism Protein Metabolism Primary Target Genes for Insulin Signaling Cell Growth and Differentiation | 2.03↑ | 1.95 | 30.3↑ |
| Pparg | NM_011146 | Target genes for PPARγ, Cell Growth and Differentiation Transcription Factors and Regulators | 0.46↓ | 3.32↑ | 0.59 |
| Ppp1ca | NM_031868 | Carbohydrate Metabolism Insulin Receptor-associated Proteins Protein Metabolism | 4.59↑ | 1.54 | 2.08↑ |
| Ptpn1 | NM_011201 | Insulin Receptor-associated Proteins Protein Metabolism | 2.62↑ | 4.66↑ | 1.65 |
| Raf1 | NM_029780 | Cell Growth and Differentiation Protein Metabolism, Transcription Factors and Regulators | 2.51↑ | 0.97 | 0.8 |
| Shc1 | NM_011368 | Cell Growth and Differentiation Insulin Receptor-associated Proteins Lipid Metabolism Protein metabolism MAPK Pathway | 3.53↑ | 1.11 | 1.64 |
| Glut-1 | NM_011400 | Carbohydrate Metabolism | 2.25↑ | 0.98 | 0.48↓ |
| Rps6ka1 | NM_009097 | MAPK Pathway, PI-3 Kinase Pathway Protein Metabolism | 2.58↑ | 1.56 | 1.31 |
| UCP1 | NM_009463 | MAPK Pathway, PI-3 Kinase Pathway Protein Metabolism | 8.4↑ | 4.76↑ | 4.44↑ |

↑ and ↓: significant upregulation and downregulation in the KK myoblast group compared with KK control group (A), KK fibroblast group (B), and C57BL group (C).

Figure 2.

| Genes | Accession no. | Categories | Fold change A | Fold change B | Fold change C |
|---|---|---|---|---|---|
| Aifm2 | NM_178058 | Apoptotic Genes | 2.45↑ | 1.52 | 1.32 |
| Aip | NM_016666 | Mitochondrial Transport Targeting Proteins to Mitochondria Mitochondrion Protein Import | 2.33↑ | 1.21 | 0.85 |
| Bcl2l1 | NM_009743 | Apoptotic Genes Mitochondrial Transport Membrane Polarization & Potential | 13.4↑ | 3.68↑ | 3.03↑ |
| Cox10 | NM_178379 | Mitochondrion Protein Import Mitochondrial Fission & Fusion | 2.31↑ | 2.52↑ | 1.1 |
| Cpt1b | NM_009948 | Mitochondrial Transport Targeting Proteins to Mitochondria Mitochondrion Protein Import | 16.33↑ | 2.06↑ | 1.72 |
| Fis1 | NM_025562 | Mitochondrial Fission & Fusion | 2.5↑ | 1.24 | 1.39 |
| Grpel1 | NM_024478 | Mitochondrial Transport Targeting Proteins to Mitochondria Mitochondrion Protein Import | 5.39↑ | 1.15 | 1.14 |
| Mfn1 | NM_024200 | Mitochondrial Fission & Fusion, Mitochondrial Localization | 2.03↑ | 0.95 | 0.86 |
| Mipep | NM_027436 | Mitochondrial Transport, Targeting Proteins to Mitochondria | 2.83↑ | 1.43 | 1.46 |
| Opa1 | NM_133752 | Inner Membrane Translocation, Mitochondrial Localization Mitochondrial Fission & Fusion | 5.13↑ | 0.95 | 2.13↑ |
| Rhot2 | NM_145999 | Mitochondrial Localization | 2.64↑ | 1.06 | 1.23 |
| Sfn | NM_018754 | Apoptotic Genes | 2.14↑ | 0.77 | 3.39↑ |
| Slc25a15 | NM_181325 | Small Molecule Transport | 2.55↑ | 0.86 | 0.91 |
| Slc25a16 | NM_175194 | Small Molecule Transport | 3.01↑ | 1.23 | 0.76 |
| Slc25a17 | NM_011399 | Small Molecule Transport | 3.16↑ | 0.89 | 1.22 |
| Slc25a20 | NM_020520 | Small Molecule Transport | 3.31↑ | 1.13 | 0.59 |
| Slc25a22 | NM_026646 | Small Molecule Transport | 3.16↑ | 2.01↑ | 2.07↑ |
| Slc25a25 | NM_146118 | Small Molecule Transport | 2.53↑ | 2.91↑ | 0.46↓ |
| Slc25a27 | NM_028711 | Small Molecule Transport | 4.26↑ | 0.92 | 1.2 |
| Stard3 | NM_021547 | Mitochondrial Transport | 2.87↑ | 2.23↑ | 1.31 |
| Taz | NM_181516 | Inner Membrane Translocation | 4.89↑ | 1.17 | 1.3 |
| Timm17b | NM_011591 | Inner Membrane Translocation | 3.39↑ | 2.19↑ | 1.17 |
| Timm22 | NM_019818 | Inner Membrane Translocation | 3.46↑ | 1.82 | 1.05 |
| Timm44 | NM_011592 | Inner Membrane Translocation | 2.31↑ | 1.09 | 1.4 |
| Tomm34 | NM_025996 | Outer Membrane Translocation | 3.27↑ | 1.56 | 1.16 |
| Tomm40 | NM_016871 | Outer Membrane Translocation | 5.13↑ | 3.46 | 1.59 |
| UCP1 | NM_009463 | Membrane Polarization & Potential Mitochondrial Transport | 8.4↑ | 4.76↑ | 4.44↑ |

↑ and ↓: significant upregulation and downregulation in the KK myoblast group compared with KK control group (A), KK fibroblast group (B), and C57BL group (C).

DISEASE PREVENTION AND ALLEVIATION BY HUMAN MYOBLAST TRANSPLANTATION

CROSS REFERENCE TO RELATED APPLICATIONS

This application is a Divisional of U.S. patent application Ser. No. 13/968,982, filed Aug. 16, 2013, which application is incorporated herein by reference in its entirety.

FIELD OF THE INVENTION

Embodiments relate to human genome therapy of disease using myoblast transfer therapy.

BACKGROUND OF THE INVENTION

Peter K. Law previously demonstrated that myoblast transfer in Duchenne muscular dystrophy (DMD) muscles produced dystrophin (a protein), and that myoblast transfer in heart muscle produced heavy myosin (another protein). Related patents and publications including Ye et al. 2009 (Diabetologia 52:1925-1934 "Skeletal myoblast transplantation . . . ") focused on determining the safety and efficacy of treating muscular dystrophies, heart muscle degeneration and diabetes.

These works relied on increased muscle strength, more myofibers, better cell structure and protein replenishment as monitoring end-points. However, they did not identify any underlying genetic/biochemical mechanism that could be used to improve therapy or used as tools for identification and selection of prophylactic or therapeutic agents such as cell transplant agents or lead drug compounds. In contrast these studies indicated that their effects operated via donor cell survival, development and functioning per se. Gene transcription and translation leading towards genetic repair have not been seriously addressed in the clinical prophylaxis and treatment of disease.

One important disease is diabetes. Diabetes is a leading cause of kidney failure and non-traumatic lower-limb amputations among adults in the world. In 2010, the United States was estimated to have spent $198 billion on diabetes treatment[1]. An estimated 285 million adults had Type II diabetes making up about 90% of diabetes cases in 2010[2]. Diabetes affects ~25% of western populations, steadily increases[3], and is an important cardiovascular disease risk factor[4]. Epidemiological and twin studies have clearly indicated a major polygenetic factor in the development of insulin resistance, a key feature of Type II diabetes, which was influenced also by environmental factors[5,6].

Previous studies demonstrated the importance of skeletal muscles in the development of insulin resistance. Mice with muscle-specific Glut-4 knockout were insulin resistant and glucose-intolerant from an early age[7]. An isolated defect in protein kinase C-λ, in muscle would induce abdominal obesity and other metabolic abnormalities[8]. In contrast, muscle-specific LKB1 (a serine/threonine kinase that is a negative regulator of insulin sensitivity) knockout increased insulin sensitivity and improved glucose homeostasis[9]. These studies suggest that defects in skeletal muscle glucose transport may be key factors in the development of insulin resistance.

Attenuated hyperglycemia and hyperinsulinemia, and improved glucose tolerance of KK mouse occurred with xeno-transplantation of human skeletal myoblasts (hSkMs)[10]. Skeletal myoblasts are mononucleated, muscle precursor cells capable of fusing with muscle fibers of different types and developing into the host phenotype[11]. Through natural fusion with KK mouse skeletal muscle fibers, implanted human myoblasts formed hybrid muscle fibers in KK mouse.

Despite this work done with diabetes, no one has identified any underlying gene transcript alterations of multiple genes or genomes. In fact, the teachings and conclusions of those works indicated that any improvement found could all be a result of donor cell survival, development and functioning without genetic repair. Accordingly, any new information and treatment modalities in this area that go beyond this basic knowledge can provide immeasurable benefit to clinical prophylaxis and treatment of disease.

SUMMARY OF THE INVENTION

There has been some progress in muscle transplant therapy over the years, beginning with the seminal work of Peter K. Law. However, there has been no specific awareness or understanding that disease symptoms of a variety of diseases could be alleviated by changes in the quality and quantity of direct transcripts of multiple genes. In an embodiment described herein, it was astonishingly shown for the first time that changes in quantity and quality of direct transcripts of multiple genes, could result in disease relief using a genetically abnormal animal model of Type-II diabetes.

It was surprisingly found that myoblast transfer in Type-II diabetic muscles produces gene transcript changes (not protein) in multiple pathways related to insulin resistance. Linking the myoblast transfer technology development from DMD, cardiomyopathy, and Type-II diabetes, this discovery unforeseeably demonstrates that myoblast transfer mediates its effect through transfer of the normal myoblast nuclei that supply the complete human genome, in addition to just replenishing the missing gene(s) or the aberrant gene(s). The replacement genes then transcribe to produce the necessary proteins or factors for genetic repair. A variety of uses of this discovery were found, including that for disease treatment, disease prevention, drug discovery, and selection of superior cells and clones for therapy.

BRIEF DESCRIPTION OF THE FIGURES

FIG. 1. Comparison of insulin signaling pathway gene transcript levels in the KK hSkM, KK control, and KK fibroblast groups at fasting state.

FIG. 2. Comparison of mitochondria gene transcript levels in the KK hSkM, KK control, and KK fibroblast groups at fasting state.

DISEASE TREATMENT AND PREVENTION

An embodiment prevents or alleviates symptoms of DMD. Another embodiment prevents or alleviates symptoms of cardiomyopathy. Yet another embodiment prevents or alleviates symptoms of Type-II diabetes.

According to a preferred embodiment, a method of treating Type II diabetes in a patient in need thereof is provided, comprising: determining or verifying Type II diabetes status of the patient; supplying a complete human genome to the patient through transfer of myoblast nuclei, comprising the steps of: a. culturing a supply of myoblasts from a muscle biopsy of a donor that is genetically normal with respect to insulin sensitivity; b. administering a therapeutically effective dosage of an immunosuppressant to the patient; c.

thereafter selecting and administering from the supply a therapeutically effective dose of myoblasts to at least one muscle of the patient, d. allowing donor myoblasts to insert their nuclei, each of which contains a full complement of normal genes into the patient's genetically abnormal muscle cells to effect genetic complementation repair; and e. allowing donor myoblasts to fuse among themselves to form genetically normal muscle fibers; whereby muscle mediated glucose homeostasis is improved, and is detected by measuring an improvement in the Type II diabetes status of the patient. In an embodiment, the cultured myoblasts are histoincompatible with the patient, and derived from a genetically normal donor. In another embodiment, the donor is selected from a genetically normal group, including but not limited to the father or a male sibling of the host.

In yet another embodiment, the cultured myoblasts are obtained from muscle biopsy of the patient before the patient has developed Type II diabetes. In yet another embodiment, the measurement of improvement in the Type II diabetes status of the patient is carried out by detecting changes in quantity or quality of direct transcripts of multiple genes that provide relief of disease symptoms.

In yet another embodiment, the therapeutically effective dose of the cultured myoblasts is approximately 50 billion cells for Type II diabetes, and this dose is administered at approximately 100 million cells per mL. In another embodiment the immunosuppressant comprises cyclosporine administered orally at 5 to 7 mg/Kg body weight per day, beginning at five days before myoblast implantation, and completely weaned at three weeks post-operatively. The cyclosporine whole blood trough level may be monitored weekly and the cyclosporine dose re-adjusted as needed to maintain a blood level of approximately 250 ng/mL until the last week when weaning begins.

An embodiment provides a method of preventing Type II diabetes in a patient, comprising: reviewing Type II diabetes potential status of the patient; supplying a complete human genome to the patient through transfer of myoblast nuclei, comprising the steps of: a. culturing a supply of myoblasts from a muscle biopsy of a donor that is genetically normal with respect to insulin sensitivity; b. administering a therapeutically effective dosage of an immunosuppressant to the patient; and c. thereafter selecting and administering from the supply a therapeutically effective dose of myoblasts to at least one muscle of the patient, d. allowing donor myoblasts to insert their nuclei, each of which contains a full complement of normal genes into the patient's abnormal muscle cells to effect genetic complementation prevention; and e. allowing donor myoblasts to fuse among themselves to form genetically normal muscle fibers; whereby muscle mediated glucose homeostasis is improved, and is detected by measuring an improvement in the Type II diabetes status of the patient. Yet another embodiment provides measuring an improvement in the Type II diabetes status of the patient.

Yet another embodiment provides a method of treating genetic disease in a host by supplying a complete genome of the host species through transfer of myoblast nuclei, comprising the steps of: a. culturing a supply of genetically normal myoblasts from muscle biopsy of genetically normal donor; b. administering a therapeutically effective dosage of an immunosuppressant to the host; and c. thereafter selecting and administering from the said supply a therapeutically effective dose of myoblasts to at least one muscle of the host, d. allowing donor myoblasts to insert their nuclei, each of which contains a full complement of normal genes into the patient's abnormal muscle cells to effect genetic complementation repair; and e. allowing donor myoblasts to fuse among themselves to form genetically normal muscle fibers; whereby detection of improvement in the host is carried out, including at least one of measurement of muscle function improvement, increase in locomotive capacity, blood ejection/vascularization, and transfer of biochemicals or ions across the muscle cell membrane.

Use in Drug Discovery

Yet another embodiment provides a drug discovery assay comprising detection of increased gene transcription of one or more of a group of 22 genes involved in insulin signaling pathway. In an embodiment, RNA transcripts are assayed and presence or quantity of RNA transcription is used to select a lead drug compound for clinical promise or use in disease (such as diabetes) prophylaxis or alleviation of symptoms. In another embodiment, bioassay of a gene transcription product activity is used to select the lead drug compound. In a preferred embodiment, the gene is one or more selected from the group consisting of Acaca, Aebp1, Cfd, Gpd-1, Jun, PPARgamma, Ptpn1 and UCP1.

These genes, gene transcripts, and proteins produced from them can be detected by a wide variety of methods as a skilled artisan readily will appreciate. Drug discovery and development involve identifying and selecting the key markers. Although a variety of genes have known involvement in the insulin signaling pathway, embodiments provide a more valuable set of genes that are surprisingly found more valuable in the myoblast therapy context and are preferred. Preferential expression of a gene listed above is particularly preferred for selecting lead compounds in drug discovery towards prevention or treatment of Type-II diabetes and other genetic diseases such as mucopolysaccharidosis.

Yet another embodiment provides a drug discovery assay comprising detection of increased gene transcription of one or more of a group of 27 genes involved in mitochondrial biogenesis and function. In an embodiment, RNA transcripts are assayed and presence or quantity of RNA transcription is used to select a lead drug compound for clinical promise or use in disease (such as diabetes) prophylaxis or alleviation of symptoms. In another embodiment, bioassay of a gene transcription product activity is used to select the lead drug compound. In a preferred embodiment, the gene is one or more selected from the group consisting of Bcl2l1, Cox10, Cpt1b, Slc25a22, Slc25a25, Stard3, Timm17b, and Tomm40.

These genes, gene transcripts, and proteins produced from them can be detected by a wide variety of methods as a skilled artisan readily will appreciate. Drug discovery and development involve identifying and selecting the key markers. Although a variety of genes have known involvement in mitochondrial biogenesis and function, embodiments provide a more valuable set of genes that are surprisingly found more valuable in the myoblast therapy context and are preferred. Preferential expression of a gene listed above is particularly preferred for selecting lead compounds in drug discovery towards prevention or treatment of Type-II diabetes, obesity, and other genetic diseases resulting from abnormal mitochondrial biogenesis and function.

Another embodiment provides a method of discovering a drug compound or cell therapy candidate useful for diabetes treatment, comprising exposure of a test compound to an in vitro, ex vitro, or in vivo group of cells, assaying for gene activity of one or more of a gene selected from the group consisting of Bcl2l1, Cox10, Cpt1b, Slc25a22, Slc25a25, Stard3, Timm17b, and Tomm40, and using a positive gene activity result to determine value of the test compound for diabetes treatment. In an embodiment the method comprises detection of gene transcripts. In an embodiment the method comprises detection of activity of a protein translated from the gene transcribed. In an embodiment the method comprises immunologic detection of a protein translated from the gene transcribed. In an embodiment the method comprises exposure of a test compound to an in vitro, ex vitro, or in vivo group of cells, assaying for gene activity of one or more of a gene selected from the group consisting of Acaca, Aebp1, Cfd, Gpd-1, Jun, PPARγ, Ptpn1, and UCP1, and using a positive gene activity result to determine value of the test compound for diabetes treatment.

Supply of Genome Via Injection of Cells

Previously, workers in this field invariably injected cells in patients using saline solution and other defined or partially defined medium as the carrier solution. The inventor surprisingly found that injection of myoblasts using the host's serum promoted cell survival and development. Clotted serum was preferred due to ease of preparation although serum with added angiogenesis factors and the use of patient plasma as medium for the injected cells also are contemplated.

It was found that a high cell concentration of the injectate, 100 million cells per mL enhances cell fusion and development after injection. The preferred technique is lower body treatment for young patients such as DMD boys between age 5 to 12, and upper body treatment for older patients such as DMD boys between age 12 to 18. Most preferred is whole body treatment ("WBT") for patients of age between 5 to 18. WBT is most preferred for Type II diabetic patients of all ages. WBT involves injecting 50 billion myoblasts into 80 large muscle groups of the patient.

In an embodiment, smaller volume sized cells are used to inject, to provide a greater DNA to cell mass ratio. In an embodiment the preferred average diameter cell sizes are 7 to 10 um. In an embodiment the average cell size is 12 um or less and can be as little as 7 um. In an embodiment a cell suspension in patient blood protein medium such as serum or plasma is provided, for use in a method of treating Type II diabetes in a patient in need thereof, the method comprising: determining or verifying Type II diabetes status of the patient; supplying a complete human genome to the patient through transfer of myoblast nuclei, comprising the steps of: a. culturing a supply of myoblasts from a muscle biopsy of a donor that is genetically normal with respect to insulin sensitivity; b. administering a therapeutically effective dosage of an immunosuppressant to the patient; and c. thereafter selecting and administering from the supply a therapeutically effective dose of myoblasts to at least one muscle of the patient, d. allowing donor myoblasts to insert their nuclei, each of which contain a full complement of normal genes into the patient's genetically abnormal muscle cells to effect genetic complementation repair; and e. allowing donor myoblasts to fuse among themselves to form genetically normal muscle fibers; whereby muscle mediated glucose homeostasis is improved, and is detected by measuring an improvement in the Type II diabetes status of the patient. In other embodiments such cell suspensions are supplied for other methods as detailed herein.

Markers for Selection of Cells Used in Transplant Therapy

In another embodiment, it was surprisingly discovered that cells, which exhibit unusually high transcription activities for certain genes provide superior benefit for cell therapy of disease, such as diabetes. In particular, such gene expression can be used for cell selection for cloning and for culture to provide enhanced cell preparations for therapy. In an embodiment, detection of gene transcription product activity is used to select the better cell or cell culture. In a preferred embodiment, the gene is one or more selected from the group consisting of Bcl2l1, Cox10, Cpt1b, Slc25a22, Slc25a25, Stard3, Timm17b, and Tomm40. In another preferred embodiment, the gene is one or more selected from the group consisting of Acaca, Aebp1, Cfd, Gpd-1, Jun, PPARgamma, Ptpn1 and UCP1. These genes, gene transcripts, and proteins produced from them can be detected by a wide variety of methods as a skilled artisan readily will appreciate.

Example: Intramuscular Implantation of Human Skeletal Myoblasts (hSkM)

This example shows an underlying gene expression profiling of the insulin signaling pathway, mitochondrial biogenesis and function, and demonstrates the effect of implementation as claimed in embodiments herein.

Diabetic KK mice were divided into three groups: KK control group with basal medium (M199) injection; KK fibroblast group with human fibroblast transplantation; KK myoblast group with hSkM transplantation. C57BL mice received hSkM transplantation as a normal control. Cells were transplanted into muscles of the hind limbs. All animals were treated with cyclosporine for 6 weeks only. Glucose tolerance tests were conducted. The mice were sacrificed in a fasting state at 12 weeks after cell transplantation. Implanted muscles were removed and processed for study of gene expression profiling.

Animals and Diets—

KK mice were purchased from Jax Lab, Maine, USA. It is a genetically obese animal model of Type-II diabetes and is characterized with hyperglycemia, hyperinsulinemia and glucose intolerance[12]. They were about 34% heavier than C57 BL mouse at 14-16 weeks of age. Mice were housed individually in plastic cages in an air-conditioned room at 25° C. with a 12-hour light and 12-hour dark cycle (light: 9:00 am to 9:00 pm) and free access to food (5K52 PMI Nutrition International LLC, USA) and water (tap water). Mouse at 14-16 weeks old were screened for hyperglycemia and used for experiment. KK mice which met the following criteria were used: (1) fasting blood glucose >6.5 mmol/L and (2) blood glucose >20 mmol/L at 30 min or 60 min, and >11 mmol/L at 2 hours during GTT[10].

Glucose Tolerance Test (GTT)—

All mice used in the study had GTT. After overnight fasting (about 16 hours), the mouse was injected intraperitoneally (i.p.) with 1 g/kg body weight of glucose diluted in distilled water (100 mg/ml). Blood samples from the tail vein were collected at 0 (before glucose injection), 30, 60 and 120 min after glucose injection. The blood glucose concentration was determined by Accu-Chek Advantage glucometer (Roche, Germany).

Culture of hSkM and Human Fibroblasts—

Human skeletal myoblasts were cultured and propagated in 225 mm$^2$ tissue culture flasks and maintained with M199 supplemented with 10% fetal bovine serum, 10 ng/ml FGF (10% M199) at 37° C. in 5% $CO_2$ incubator until confluent. The purity and uniformity of hSkM culture were assessed for desmin and CD56 expression as described previously. Human fibroblasts were obtained from the laboratory of Associate Professor Toan Thang Phan, Department of Surgery, NUS, Singapore.

Cell Labelling and Transplantation—

Cells were labelled with 4, 6-diamidino-2-phenylindole (DAPI) (Sigma, USA) overnight before cell transplantation[10].

KK mice meeting the criteria for diabetes were randomly assigned into three groups: KK control group (n=8): receiving 1.5 ml M199 only, KK fibroblast group (n=8): receiving 1.5 ml M199 containing 3×10[7] human fibroblasts, and KK myoblast group (n=8): receiving 1.5 ml M199 containing 3×10[7] hSkMs. C57BL mouse was used as a normal control to determine any side effects related to hSKM transplantation and received 1.5 ml M199 containing 3×10[7] hSkMs. A total of 20 injections were injected into the bilateral muscle of the anteromedial aspect of the thigh, muscles of the posterior aspect of the leg, and muscles of the gluteal region of mice under anesthesia. After injection, mice were returned to their cage for recovery. All animals received cyclosporine treatment (10 mg/kg/day) for 3 days before treatment until 6 weeks after treatment. After blood sampling, animals were sacrificed at 12 weeks. Immunohistochemical studies—The DAPI+ cryo-sections from mouse skeletal muscles that were explanted at 12 weeks after cell transplantation were immunostained for expression of dystrophin to determine the integration of hSkM nuclei into mouse skeletal muscle fibers[10]. Briefly, the tissue sections were fixed in 100% methanol at −20° C. for 20 min followed by incubation with 0.1% Triton-100 for 10 min at 4° C. After blocking, the primary antibody solutions containing rabbit anti-dystrophin (Sc-15376, Santa Cruz, USA) antibody at 1:50 dilution was applied on the samples and incubated for 1 hour at room temperature. Following this, goat anti-rabbit IgG conjugated with Fluorescein isothiocyanate (FITC) (F-4890, Sigma, USA) at 1:200 dilution was applied for 1 hour. After thorough wash, the samples were counter-stained with propidium iodine and observed under Olympus BX41 (Olympus, Japan) fluorescent microscope and images were recorded using a digital camera with Olympic Micro Image (Olympus, Japan).

Isolation of Muscle Tissues and Total RNA Preparation—

After sacrificing, mouse skeletal muscles of the anteromedial aspect of the thigh were immediately separated, collected and stored in liquid nitrogen. Total RNA was extracted from frozen muscle samples with Trizol reagent (Invitrogen, USA) according to manufacturer's instructions. The concentration and purity of RNA was determined by Nanodrop. DNase I (Fermentas, USA) was used to remove DNA contamination from total RNA. cDNA was synthesized using Maxima® First Strand cDNA Synthesis Kit (Fermentas, USA) from 1 µg total RNA. 1 µL (~1 µg) cDNA was used for one array plate. The real-time PCR cycle was performed according to RT[2] Profiler™ PCR Array User Manual as per instruction. The gene expression level changed ≥2 folds would be considered significantly increased between groups, while the gene expression level changed ≤0.5 fold would be considered as significantly reduced between groups. The gene expression level would be further confirmed and quantified by quantitative PCR (QPCR) using cDNA. To confirm gene expression level, Maxima® SYBR Green qPCR Master Mix (2X) (Fermentas, USA) was used. Primers were designed using Primer Premier 5 software (Premier Biosoft, USA). Sequences were able to be obtained upon request. The QPCR thermal cycling protocol for 40 cycles was programmed as following: 1 cycle of initial denaturation for 10 min, then denaturation at 95° C. for 15 seconds, annealing for 30 seconds and extension at 72° C. for 30 seconds.

PCR array kits for genes expression profiles in skeletal muscle of mouse insulin pathway and mitochondrial biogenesis and function were purchased from SABiosciences, USA. The Mouse Insulin Signalling Pathway RT[2] Profiler™ PCR Array (Cat PAMM-030, QIAGEN-SAbiosciences, USA) profiles the expression of 84 genes related to the role of insulin-responsive genes. Insulin mediates a wide spectrum of biological responses associated with glucose uptake, glycogen, lipid and protein synthesis, transcriptional activation, cell growth and differentiation.

The Mouse Mitochondria RT[2] Profiler™ PCR Array (PAMM-087, QIAGEN-SAbiosciences, USA) profiles the expression of 84 genes involved in the biogenesis and function of the cell's powerhouse organelle. The genes monitored by this array include regulators and mediators of mitochondrial molecular transport of not only the metabolites needed for the electron transport chain and oxidative phosphorylation, but also the ions required for maintaining the mitochondrial membrane polarization and potential important for ATP synthesis. Metabolism and energy production are not the only functions of mitochondria. Intrinsic apoptosis pathway genes activated by intracellular damage signalling are also included in this array.

Statistical Analysis:

Statistical analysis was performed using SPSS 20. All data are presented as the mean±the standard error meaning. The area under the curve of the 4-point glucose measurements was used to compare the difference among three groups by ANOVA. A probability value of $p<0.05$ was considered a significant difference between groups.

Results:

hSkMs survived extensively in host muscles at 12 weeks after cell transplantation. Glucose tolerance test showed a significant decrease of blood glucose in mice of the KK myoblast group compared to the KK control and the fibroblast groups. Transcriptional patterns of the insulin signalling pathway showed alterations in the KK myoblast group as compared with the KK control group (23 genes), the KK fibroblast group (8 genes), and the C57BL group (8 genes). Transcriptional patterns of mitochondrial biogenesis and function also showed alterations in the KK myoblast group as compared with the KK control group (27 genes), the KK fibroblast group (9 genes), and the C57BL group (6 genes).

It was surprisingly found, and for the first time, that hSKM transplantation resulted in changes of gene transcripts with multiple genes involved in the insulin signalling pathway, and in mitochondrial biogenesis and function. This was accompanied with an improvement in glucose tolerance and reduced hyperglycemia in the diabetic KK mouse.

Body Weight—

The mean body weights of the four animal groups at 12 weeks after treatment were: KK control group=32.3±1.3 gram, KK fibroblast=33.1±1.7 gram, and KK myoblast group=30.4±1.2 gram, and C57BL group=22.9±0.5 gram. The body weight of KK mice was significantly heavier than that of C57BL mice (p<0.05 for all). Although there was a tendency of a decreased body weight in the KK myoblast group, no significant difference was found between any two KK groups.

Glucose Homeostasis and Cell Integration Analyses—

Glucose homeostasis results of mouse at 12 weeks after treatment: HbA1c of KK myoblast group was significantly reduced as compared with KK control and KK fibroblast. However, it was still significantly higher than that of C57BL group, which served as a normal control. GTT showed that KK myoblast group had significantly reduced plasma glucose concentration during GTT and similar to that of C57BL group. (vs KK control and fibroblast p<0.05, & vs any KK group: p<0.05).

hSkM nuclei integrated into host muscle fibers: DAPI labeling of hSkMs nuclei showed 100% labeling efficiency. Survival of DAPI-positive hSkMs in mouse skeletal muscle immunostaining for dystrophin protein expression was determined. The same tissue was counter stained with propidium iodine to show all nuclei. An overlay of images of these two conditions showed integration of hSkM nuclei into mouse skeletal muscle.

Improvement of HbA1c and Glucose Tolerance Test—

Glycosylated haemoglobin assay demonstrated that the KK myoblast group mice achieved significantly better glucose control after hSkM transplantation. At 12 weeks after treatment, HbA1c of KK myoblast group was significant lower than those of KK control and fibroblast groups (p<0.05 for both). HbA1c of C57BL group was significantly lower than any KK group (p<0.05 for all).

A significant decrease in blood glucose concentration was observed in the KK myoblast group. At 12 weeks after transplantation, KK control and fibroblast group animals had severe hyperglycemia and glucose intolerance. By contrast, KK myoblast group mice showed a significant reduction in blood glucose as compared with KK control and fibroblast groups (p<0.05 for both), and reached to almost similar level as C57BL group (p>0.05).

Survival and Integration of hSkMs in Host Mouse Skeletal Muscle—

The labelling efficiency of hSkMs was 100% for DAPI. Extensive survival of hSkM shown as DAPI+ nuclei was found in mouse skeletal muscle at 12 weeks after cell transplantation.

Immunostaining of DAPI+ tissue for dystrophin expression showed that hSkM nuclei were co-localized with host nuclei in the same muscle fibers, suggesting that hSkM integrated into host skeletal muscle fibers to form hybrid muscle fibers as dystrophin lineated the boundary of skeletal muscle fibers.

Array Analysis of Gene Expression of Insulin Signaling Pathway in Anteromedial Muscle of the Thigh KK Myoblast Group Versus KK Control Group Mice in KK myoblast group compared with KK control group had 22 gene transcripts increased and 1 decreased, which was 27.4% of 84 genes screened (FIG. 1). Most of the 22 increased genes belonged to protein metabolism (13), cell growth and differentiation (9), MAPK pathway (6), and insulin receptor-associated proteins (6), transcription factors and regulators (4), carbohydrate metabolism (4) functional groups. The only gene that had a reduced transcript was the target gene for peroxisome proliferator activated receptor gamma (PPARγ). This is a novel and interesting finding.

KK Myoblast Group Versus KK Fibroblast Group

Mice in KK myoblast group compared with KK fibroblast group had 8 (9.5% of 84) gene transcripts increased (FIG. 1). The 8 genes belonged to protein metabolism (3), cell growth and differentiation (2), insulin receptor-associated proteins (1), transcription factors and regulators (3) and target genes for PPARγ (3) functional groups.

KK Myoblast Group Versus C57BL Group

Compared with C57BL group, mice in KK myoblast group had 8 gene transcripts changed (FIG. 1). Among these, 7 gene transcripts increased and 1 decreased. Most of the 7 increased genes belonged to protein metabolism (4), MAPK pathway (2), carbohydrate metabolism (3), and PI-3 kinase pathway (2) functional groups. The only gene that had decreased transcription was Glut-1. There was no change in the PPARγ gene transcript.

Array Analysis of Gene Expression of Mitochondrial Biogenesis and Function in Anteromedial Muscle of the Thigh KK Myoblast Group Versus KK Control Group Compared with KK control group, KK myoblast group had 27 (32.1% of 84) gene transcripts increased (FIG. 2). Most of the 27 genes belonged to small molecule transport (7), mitochondrial transport (7), inner membrane translocation (5), targeting proteins to mitochondria (4), mitochondrion protein import (4), mitochondrial fission and fusion (4), mitochondrial localization (3 increased), and out membrane translocation (2), and membrane polarization & potential (2) functional groups.

KK Myoblast Group Versus KK Fibroblast Group

Compared with the KK fibroblast group, the KK myoblast group had only 9 (10.7% of 84) gene transcripts increased (FIG. 2). Most of the 9 genes belonged to small molecule transport (2), mitochondrial transport (4), inner membrane translocation (1), targeting proteins to mitochondria (1), mitochondrion protein import (2), mitochondrial fission and fusion (1), out membrane translocation (1), and membrane polarization & potential (2) functional groups. No gene that belonged to mitochondrial localization functional group showed any significant difference between KK myoblast and KK fibroblast groups.

KK Myoblast Group Versus C57BL Group

Compared with the C57BL group, the KK myoblast group had less mitochondrial gene transcripts changed (FIG. 2). Five gene transcripts increased and 1 gene transcript decreased. The 5 genes belonged to small molecule transport (1), mitochondrial transport (2), inner membrane translocation (1), targeting proteins to mitochondria (4), mitochondrion protein import (4), mitochondrial fission and fusion (1), mitochondrial localization (1 increased), and out membrane translocation (2), and membrane polarization & potential (2) functional groups. The only gene that had decreased transcription was Slc25a25, which is a small molecular transport gene.

No gene that belongs to targeting proteins to mitochondria, mitochondrion protein import and out membrane translocation etc., functional groups showed any significant difference between KK myoblast and C57BL groups.

The example surprisingly shows that gene profiles of insulin signaling pathway and mitochondrial biogenesis and function were changed in skeletal muscles of KK mouse after hSkM transplant, as documented changes in gene transcripts. There are 23 (27.4%) and 27 (32.1%) gene transcripts, of insulin signaling pathway and mitochondrial biogenesis and function, respectively, changed in skeletal muscle of KK mouse after hSkM transplantation as compared with KK control mouse. However, the gene number reduced to 8 (9.5%) and 9 (10.7%) as compared with KK fibroblast group, and 8 (9.5%) and 6 (7.1%) as compared with C57BL group. These indicated that hSkM transplantation into KK mouse skeletal muscle changed the expression level of genes involved in the insulin signaling pathway and in mitochondrial biogenesis and function. Without wishing to be bound by any one theory or "gist" for this embodiment, it is believed that these changes directly and indirectly contribute to the reduced hyperglycemia and improved glucose tolerance.

These results show that hSkM transplantation achieved better glucose homeostasis and improved glucose tolerance, which were accompanied with extensive survival of hSkMs in KK mouse skeletal muscle at 12 weeks after cell transplantation using a transient immune-suppression treatment. The hSkM nuclei integrated into host skeletal muscle fibers. The fusion between donor myoblasts with host skeletal muscle fibers formed hybrid muscle fibers. Without wishing to be bound by any one theory or "gist" for this embodiment, it is believed that this could help the donor hSkM to escape host immuno-rejection after withdrawal of cyclosporine treatment as mature skeletal muscle fibers do not express mayor histocompatibility complex class 1 antigens. The donor nuclei may also co-express exogenous genes together with host genes in the hybrid muscle fibers. Results of the example further demonstrate that implantation of normal hSkM could increased expression level of 22 genes involved in insulin signalling pathway and 27 genes involved in mitochondrial biogenesis and function.

It was found that 23 genes of insulin signaling pathway changed in KK myoblast group as compared with KK control group: 22 increased and 1 decreased. Except secondary effector target genes for insulin signaling functional group, all other functional groups have genes significantly changed. Prominently, half of these genes (56.55% of 23 genes) are involved in protein metabolism. Most of them are multi-functional and are involved in other functional groups. For example, Cebpa, Frs2, Hras 1, Jun, Leptin, Raf, and Shc1 are not only involved in cell growth and differentiation, but are also involved in protein metabolism.

Compared with the KK fibroblast group, 8 gene transcripts were increased in KK myoblast group: Acaca, Aebp1, Cfd, Gpd-1, Jun, PPARγ, Ptpn1, and UCP1. Compared with C57BL group, 7 gene transcripts increased and 1 decreased in KK myoblast group: Braf, Frap1, Gpd-1, Igf2, Leptin, Ppp1ca, and UCP1 increased, while Glut-1 decreased. We found that only KK mice that received hSkM transplantation had significantly improved hyperglycemia, glucose tolerance and insulin resistance as compared with not only KK control mice, but also KK mice that received human fibroblast transplantation. However the KK myoblast group did not develop the same glucose homeostasis as the C57BL group. Thus, it is surprisingly seen that Acaca, Aebp1, Cfd, Gpd-1, Jun, PPARγ, Ptpn1, and UCP1 are more important than other remaining 15 genes contributing to glucose homeostasis, particularly in the context of cell transplant therapy. All the remaining 15 gene transcript levels were similar between KK myoblast and KK fibroblast groups.

Twenty seven genes of mitochondrial biogenesis and function increased in KK myoblast group as compared with KK fibroblast group. All functional groups had genes that significantly changed in the KK myoblast group. Half of the genes (51.9% of 27) were involved in small molecule transport (7) and mitochondrial transport (7). Except for genes of small molecule transport, inner and outer membrane translocations, most others are also multi-functional and are involved in other functional groups. For example, Aip, Cpt1b, and Grpel1 are not only involved in mitochondrial transport, but are also involved in mitochondrial protein import and targeting proteins to mitochondria.

When compared with the KK fibroblast group, the KK myoblast group showed gene transcript increases in 9 genes: Bcl2l1, Cox10, Cpt1b, Slc25a22, Slc25a25, Stard3, Timm17b, Tomm40, and UCP1. When compared with the C57BL group, the KK myoblast group showed gene transcript increases in 5 genes: Bcl2l1, Opa1, Sfn, Slc25a22, and UCP1, and gene transcript decrease in 1 gene: Slc25a25. Only the KK mice that received hSkM transplantation were found to have significantly improved hyperglycemia, glucose tolerance and insulin resistance as compared with the KK control and the KK fibroblast mice. Nonetheless, they did not develop the same glucose homeostasis as C57BL mice. Thus it is surprisingly found that Bcl2l1, Cox10, Cpt1b, Slc25a22, Slc25a25, Stard3, Timm17b, Tomm40 are more important than the remaining 19 genes contributing to glucose homeostasis, as the remaining 19 gene transcript levels were similar between KK myoblast and KK fibroblast groups.

The results show that SkM transplantation supplements missing genes that are involved in glucose transport and metabolism. The expression levels of multi-genes involved in insulin signalling pathway and mitochondria biogenesis and function were significantly increased. These changes contributed directly and indirectly to enhance glucose transportation and metabolism in skeletal muscles. This, in turn, caused reduced hyperglycemia and hyperinsulinemia and ameliorated the diabetic phenotype of the KK mice.

Accordingly, it is surprisingly shown that xeno-transplantation of normal hSkM into limb skeletal muscles of KK mouse up-regulated expression of multiple genes involved in the insulin signalling pathway and in mitochondria biogenesis and function. This is accompanied with improved glucose tolerance and reduced hyperglycemia in the KK mouse. The specific genes discovered in this context are useful tools for monitoring disease (particularly diabetes) onset, progression, and possible and actual therapy by cellular augmentation. Detection of one or more of these genes is particularly helpful before, during and after treatment with disease alleviation agents such as cellular augmentation such as that described here. These genes and their products are also useful for selection of superior cell clones for use in the emerging field of cellular therapeutics. A skilled artisan readily will appreciate ways to select cells bred for disease treatment and prophylaxis, using one or more of the particular genes described here.

The claims are exemplary and not limiting. A skilled artisan can determine additional related embodiments based on the disclosure herein, and space considerations preclude a further exhaustive listing of such embodiments that are readily apprehended upon reading this disclosure. The following references are specifically incorporated by reference in their entireties. Particularly incorporated are the methods and materials disclosed for obtaining and growing cells, and assaying biochemical (including protein and DNA/RNA) and cellular markers. Most particularly, each clinical step, procedure and material use for muscle cell biopsy, culture, identification and use described in references 10 and 13 specifically are incorporated by reference.

REFERENCES

1. Zhang P, Zhang X, Brown J, Vistisen D, Sicree R, Shaw J, Nichols G. Global healthcare expenditure on diabetes for 2010 and 2030. Diabetes research and clinical practice. 2010; 87:293-301. 2. Vijan S. Type 2 diabetes. Annals of internal medicine. 2010; 152:ITC31-15; quiz ITC316. 3. Mokdad A H, Ford E S, Bowman B A, Nelson D E, Engelgau M M, Vinicor F, Marks J S. The continuing increase of diabetes in the us. Diabetes care. 2001; 24:412. 4. Haffner S M, Lehto S, Ronnemaa T, Pyorala K, Laakso M. Mortality from coronary heart disease in subjects with type 2 diabetes and in nondiabetic subjects with and without prior myocardial infarction. The New England journal of medicine. 1998; 339:229-234. 5. Guillausseau P J, Tielmans D, Virally-Monod M, Assayag M. Diabetes: From phenotypes to genotypes. Diabetes & metabolism. 1997; 23 Suppl 2:14-21. 6. Stern M P. Genetic and environmental influences on type 2 diabetes mellitus in mexican americans. Nutrition reviews. 1999; 57:566-70. 7. Zisman A, Peroni O D, Abel E D, Michael M D, Mauvais-Jarvis F, Lowell B B, Wojtaszewski J F, Hirshman M F, Virkamaki A, Goodyear L J, Kahn C R, Kahn B B. Targeted disruption of the glucose transporter 4 selectively in muscle causes insulin resistance and glucose intolerance. Nature medicine. 2000; 6:924-928. 8. Farese R V, Sajan M P, Yang H, Li P, Mastorides S, Gower W R, Jr., Nimal S, Choi C S, Kim S, Shulman G I, Kahn C R, Braun U, Leitges M. Muscle-specific knockout of pkc-lambda impairs glucose transport and induces metabolic and diabetic syndromes. The Journal of clinical investigation. 2007; 117:2289-2301. 9. Koh H J, Arnolds D E, Fujii N, Tran T T, Rogers M J, Jessen N, Li Y, Liew C W, Ho R C, Hirshman M F, Kulkarni R N, Kahn C R, Goodyear U. Skeletal muscle-selective knockout of lkb1 increases insulin sensitivity, improves glucose homeostasis, and decreases trb3. Molecular and cellular biology. 2006; 26:8217-8227. 10. Ye L, Lee K O, Su L P, Toh W C, Haider H K, Law P K, Zhang W, Chan S P, Sim E K. Skeletal myoblast transplantation for attenuation of hyperglycaemia, hyperinsulinemia and glucose intolerance in a mouse model of type 2 diabetes mellitus. Diabetologia. 2009; 52:1925-1934. 11. Campion D R. The muscle satellite cell: A review. International review of cytology. 1984; 87:225-251. 12. Iwatsuka H, Shino A, Suzuoki Z. General survey of diabetic features of yellow kk mice. Endocrinologia japonica. 1970; 17:23-35. 13. Ye L, Haider H, Tan R, Toh W, Law P K, Tan W, Su L, Zhang W, Ge R, Zhang Y, Lim Y, Sim E K. Transplantation of nanoparticle transfected skeletal myoblasts overexpressing vascular endothelial growth factor-165 for cardiac repair. Circulation. 2007; 116:I113-120. 14. Karpati G, Pouliot Y, Carpenter S. Expression of immunoreactive major histocompatibility complex products in human skeletal muscles. Annals of neurology. 1988; 23:64-72.

What is claimed is:

1. A method of treating type II diabetes of a subject in need thereof, comprising the steps of:
    (a) culturing a supply of genetically normal myoblasts from skeletal muscle biopsy of a donor that is genetically normal with respect to insulin sensitivity, to provide cultured myoblasts;
    (b) administering a therapeutically effective dosage of an immunosuppressant to the subject; and
    (c) after the step (b), injecting a therapeutically effective dose of the cultured myoblasts of the step (a) to at least one skeletal muscle of the subject wherein the cultured myoblasts are injected together with a carrier,
    (d) allowing the cultured myoblasts to insert their nuclei, each of which contain a full complement of normal genes, into the subject's abnormal skeletal muscle cells; and
    (e) allowing the administered cultured myoblasts to fuse among themselves to form genetically normal muscle fibers of the subject,
    wherein the carrier of step (c) is serum or plasma of the subject; and
    wherein the treating type II diabetes is an improvement in glucose tolerance and a reduced hyperglycemia in the subject.

2. The method of claim 1, wherein said cultured myoblasts are histoincompatible with the subject.

3. The method of claim 2, wherein the donor is biological father or a male sibling of the subject.

4. The method of claim 1, wherein donor is the subject.

5. The method of claim 1, which further comprising (f) detecting changes in the quantity or quality of direct transcripts of genes involved in the insulin signaling pathway and in mitochondrial biogenesis and function.

6. The method of claim 5, wherein the genes are selected from the group consisting of Bcl2l1 (BCL2-Like 1), Cox10 (cytochrome c oxidase assembly factor), Cpt1b (carnitine palmitoyltransferase i), Slc25a22 (solute carrier family 25 (mitochondrial carrier, glutamate), member 22), Slc25a25 (solute carrier family 25 (mitochondrial carrier, glutamate), member 25), Stard3 (start domain-containing protein 3), Timm (translocase of inner mitochondrial membrane) 17b, Tomm40 (translocase of outer mitochondrial membrane 40), Acaca (acetyl-coa carboxylase-alpha), Aebp1 (ae-binding protein 1), Cfd (complement factor d), Gpd-1 (glycerol-3-phosphate dehydrogenase 1), Jun (v-jun avian sarcoma virus 17 oncogene homolog), PPARγ (peroxisome proliferator-activated receptor-gamma), Ptpn1 (protein-tyrosine phosphatase, nonreceptor-type, 1), and UCP1 (uncoupling protein 1).

7. The method of claim 1, wherein said therapeutically effective dose of the cultured myoblasts is approximately 50 billion cells, with said dose being administered at dosage of approximately 100 million cells per mL of the carrier.

8. The method of claim 1, wherein said immunosuppressant comprises cyclosporine and is administered orally at 5 to 7 mg/Kg body weight per day, beginning at five days before myoblast implantation, and terminating at three weeks post-operatively.

9. The method of claim 8, which further comprises monitoring weekly a cyclosporine whole blood trough level and adjusting a cyclosporine dose to maintain at approximately 250 ng/mL until the last week when weaning begins.

\* \* \* \* \*